(12) United States Patent
Desmonceaux et al.

(10) Patent No.: US 6,905,841 B2
(45) Date of Patent: Jun. 14, 2005

(54) **ENZYMATIC SUBSTRATES FOR DETECTING *PSEUDOMONAS AERUGINAS***

(75) Inventors: Mireille Desmonceaux, Lagnieu (FR); Daniel Monget, Saint-Sorlin-en-Bugey (FR)

(73) Assignee: Biomerieux S.A., Marcy l'Etoile (FR)

( * ) Notice: Subject to any disclaimer, the term of this patent is extended or adjusted under 35 U.S.C. 154(b) by 239 days.

(21) Appl. No.: 10/148,327

(22) PCT Filed: Dec. 6, 2000

(86) PCT No.: PCT/FR00/03398

§ 371 (c)(1), (2), (4) Date: May 29, 2002

(87) PCT Pub. No.: WO01/42491

PCT Pub. Date: Jun. 14, 2001

(65) Prior Publication Data

US 2003/0044877 A1 Mar. 6, 2003

(30) Foreign Application Priority Data

Dec. 6, 1999 (FR) .............................. 99 15312

(51) Int. Cl.⁷ ............................................... C12Q 1/04
(52) U.S. Cl. .......................................... 435/34; 435/24
(58) Field of Search .............................. 435/18, 24, 29, 435/34, 325, 395, 404

(56) References Cited

U.S. PATENT DOCUMENTS

| | | | |
|---|---|---|---|
| 5,571,684 A | * 11/1996 | Lawrence et al. | ............. 435/18 |
| 5,610,029 A | * 3/1997 | Ehrenfeld et al. | ............. 435/34 |
| 6,046,016 A | * 4/2000 | Orenga | ........................ 435/24 |
| 6,472,167 B1 | * 10/2002 | Townsend et al. | ............. 435/34 |

FOREIGN PATENT DOCUMENTS

| WO | WO 94/21816 | * 9/1994 | ............ C12Q/1/34 |
|---|---|---|---|
| WO | WO 99 51767 A | 10/1999 | |

OTHER PUBLICATIONS

Kasafirek,, et al., "Role of Amino Acid Residues in Chromogenic Substrates Cleaved by Pancreatic Elastase," 52 *Collect. Czech. Chem. Commun.* 1625–33 (1987).

Suszkiw, et al., "Brain Aminoacyl Arylamidase. Further Purification of the Soluble Bovine Enzyme and Studies on Substrate Specificity and Possible Active–Site Residues," 9 *Biochemistry*, 4008–4017 (1970).

Vermelho, et al., "Detection of Extracellular Proteases From Microorganisms on Agar Plates," 91 *Memorias Do Instituto Oswaldo Cruz* 755–760 (1996).

Louis et al., "Spectrophotometric Assay For Amidolytic Activity of Alkaline Protease From *Pseudomonas Aeruginosa*," 345 *Analytica Chimica Acta* 219–225 (1997).

Besson et al., "Synthetic Peptide Substrates For a Conductimetric Assay of *Pseudomonas Aeruginosa* Elastase," 237 *Analytical Biochemisty* 216–223 (1996).

Saulnier et al., "Conductimetric Assay of Elastase in the Supernatants of Cultures of *Pseudomonas–Aeruginosa* Strains," 247 *Analytica Chimica Acta* 79–82 (1991).

* cited by examiner

*Primary Examiner*—Ralph Gitomer
(74) *Attorney, Agent, or Firm*—James C. Lydon

(57) ABSTRACT

An enzyme substrate which includes a target portion and a marker portion, hydrolysis of the substrate leading to separation of the target portion from the marker portion, and the target portion being specific for the enzyme activity being assayed. A formulation containing at least one such substrate, and a method for detecting the bacterial species *Pseudomonas aeruginosa* is also disclosed. The target portion of the substrate is specific for β-alanine aminopeptidase activity and the marker portion is a compound which reveals whether a hydrolysis reaction has taken place or not. The invention is particularly applicable in the field of diagnosis.

15 Claims, No Drawings

ENZYMATIC SUBSTRATES FOR DETECTING PSEUDOMONAS AERUGINAS

This application is a U.S. National Stage of International application PCT/FR00/03398, filed Dec. 6, 2000, and published on Jun. 14, 2001 in the French Language which claims priority to French Application 99/15312 filed Dec. 6, 1999.

This invention concerns a substrate which can be used in a test based on detection of the activity of the enzyme β-alanine aminopeptidase. It also concerns a formulation containing at least one such substrate, and a method for detecting the bacterial species *Pseudomonas aeruginosa*.

For many years, special substrates have been used to determine whether enzymatic activities typical of microorganisms are present or not. Through the use of specific substrates, it is possible-on the basis of whether a reaction takes place or not-to characterize the nature of a genus of microorganisms, or distinguish between different strains and/or species belonging to a given genus.

Synthetic enzyme substrates are made up of two different parts: the first part is specific to the enzyme activity being tested for and will hereafter be referred to as the target part; the second part acts as a marker and will hereafter be referred to as the marker part.

Such special substrates may be either fluorescent or chromogenic. In fact, the second marker part or the product of its reaction with one or more other compounds becomes fluorescent or chromogenic when it is no longer associated with the first target part (in this context, refer to Patent Application PCT/FR99/00781 filed on behalf of the applicant).

Prior art does not provide any simple test to characterize the species *Pseudomonas aeruginosa*, although this species—by virtue of its potent pathogenicity, its widespread high incidence, and its role in many nosocomial infections—is still among the most commonly sought for.

In accordance with this invention, a range of substrates based on β-Alanine is proposed, all of which will facilitate reliable detection of *Pseudomonas aeruginosa*. The invention also concerns a formulation containing at least one such substrate, and a method for detecting *Pseudomonas aeruginosa*.

Certainly, β-Alanine is a we characterized substrate. Thus, in a paper by Kasafirek, Evzen et al., entitled "Role of amino acid residues in chromogenic substrates cleaved by pancreatic elastase", Collect. Czech. Chem. Commun. (1987), 52(6), 1625–33, mention is made of chromogenic substrates such as β-Alanine p-Nitroaniline (synthetic pathway given on page 1631).

In an article published by J. B. Suszkiw, A. S. Brecher, on "Brain Aminoacyl Arylamidase. Further Purification of the Soluble Bovine Enzyme and Studies on Substrate Specificity and Possible Active-Site Residues", Biochemistry, vol. 9, no. 20 (1970), pages 4008–4017, a method is proposed for the purification from bovine brain tissue of a soluble Arylamidase, β-Alanine β-naphthylamine (synthetic pathway given in paragraph 2 on age 4010).

In this case too, the target is completely different from that which we are proposing.

Patent application WO-A-96/40980 describes a method and a formulation for detecting the existence of and measuring the overall density of viable bacteria in foodstuffs. This involves using various substances, including N-Acetyl-L-phenylalanyl-L-arginine-7-amido-4-methylcoumarin hydrochloride.

However, the main objective in WO-A-96/40980 is not specificity for a single species (e.g. *Pseudomonas aeruginosa*) but rather to assay all bacteria present. In order to do so many different substrates are used, none of which are capable of detecting *Pseudomonas aeruginosa*-specific β-alanine aminopeptidase activity because the list given includes many different species and, with respect to the genus Pseudomonas, only two species are mentioned, namely *Pseudomonas fluorescens* and *Pseudomonas putida*, the former being easily distinguished because *Pseudomonas aeruginosa* naturally gives green colonies due to its production of pyoverdine, and the latter species does not express any βalanine aminopeptidase activity.

To this effect, this invention concerns an enzyme substrate made up of one target part and one marker part, hydrolysis of this substrate leading to separation of the marker part and the target part, said target part being specific for the enzyme activity being assayed, characterized in that this target part is acted upon by the enzyme β-alanine aminopeptidase derived from at least one *Pseudomonas aeruginosa* microorganism, and the marker part is a molecule which reveals whether a hydrolysis reaction has taken place or not.

According to a preferred embodiment, the target part consists of β-Alanine or a derivative thereof, and the marker part is a fluorescent or chromogenic molecule.

Still according to a preferred embodiment, the substrate has the following formula:

$$H_2N—CH_2—CH_2—CO—NH—R,$$

in which $H_2N—CH_2—CH_2—CO—$ is the target part and $—NH—R$ is the chromogenic or fluorescent marker part of the substrate.

Again according to a preferred embodiment, the marker part consists of:
β-Naphthylamine,
An aminomethylcoumarin, such as 7-amino-4-methylcoumarin,
an Aminobenzene derivative, such as 4-amino-2,6-dichlorophenol,
p-Nitroaniline, or
2-amino-indoxyl or 3-amino-indoxyl.

The invention also concerns a formulation for detecting at least one strain and/or species of microorganism which includes at least one substrate as described above plus a culture medium.

According to a modification, a formulation for detecting at least one strain and one species of microorganism, or at least two strains or two species of microorganism, which contains at least one substrate as described above, plus at least one other substrate and a culture medium.

According to a modification, the culture medium contains a developer.

In this case, the developer in the culture medium is:
a diazonium salt, when the marker released is β-Naphthylamine, or
3,5-dihydroxy-2-naphthoic acid, when the marker part released is an Aminobenzene derivative.

Preferably, the formulation is in the form of a liquid broth or a semi-solid agar medium.

Finally, the invention concerns a method for detecting the bacterial species *Pseudomonas aeruginosa*, the method consisting in:
bringing at least one substrate capable of detecting β-alanine aminopeptidase enzyme activity into contact with a sample suspected of containing at least one *Pseudomonas aeruginosa* microorganism, and
monitoring for the appearance of colored and/or fluorescent reactions.

According to a modification, the detection method for the bacterial species *Pseudomonas aeruginosa* consists in:

bringing at least one substrate capable of detecting β-alanine aminopeptidase enzyme activity into contact with a sample suspected of containing at least one *Pseudomonas aeruginosa* microorganism, bringing at least one substrate capable of detecting the activity of some enzyme other than β-alanine aminopeptidase into contact with a sample suspected of containing at least one microorganism other than *Pseudomonas aeruginosa*, this other enzyme activity making it possible to distinguish *Pseudomonas aeruginosa* from this other microorganism, and monitoring for the appearance of colored and/or fluorescent reactions.

In both examples above, the culture medium is semi-solid.

In this case, some product is added to the culture medium to inhibit the diffusion of the color(s) obtained.

This invention concerns the exploitation of a biological parameter which is specific to most strains of the bacterial species *Pseudomonas aeruginosa*, namely β-alanine aminopeptidase activity. This activity is only found in a very small number of other species.

The invention consists in combining a suitable marker part with a target part which is specific for this enzyme, namely β-Alanine. Suitable marker parts to reveal this activity are already in existence but they have not hitherto been used in the detection of *Pseudomonas aeruginosa* because the link between this species and this enzyme activity has never previously been described.

Thus, the first family of substrates consists of molecules with a Naphthylamine as the marker part. One of the formulae—corresponding to the substrate β-alanyl-β-naphthylamide—is:

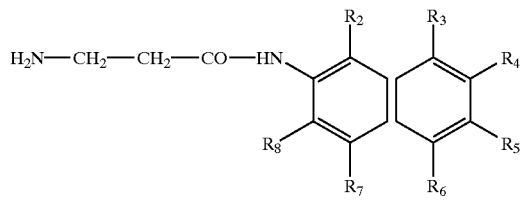

in which $R_2$, $R_3$, $R_4$, $R_5$, $R_6$, $R_7$, and $R_8$ represent an atom of hydrogen, bromine, chlorine or iodine, or a group such as —OH, —$CH_3$, —$CH_2CH_3$, —$OCH_3$, —$OCH_2CH_3$ or COOH at each of these positions. β-Naphtylamine can be used to detect β-alanine aminopeptidase activity, as described in the Doctoral/Engineering Dissertation defended by Mr. Daniel Monget at the Université Claude Bernard—Lyon I on Jul. 4, 1978 (Order n° 297). Since this type of molecule is colorless, members of this family have to be used in conjunction with some kind of developer, such as a diazonium salt.

The second family of substrates in the background art is constituted by compounds in which the marker part is based on aminomethylcoumarin which becomes fluorescent on release from the target part. The general formula for this family of substrates can be deduced from the following specific formula which is that of β-Alanyl-7-amido-4-methylcoumarin:

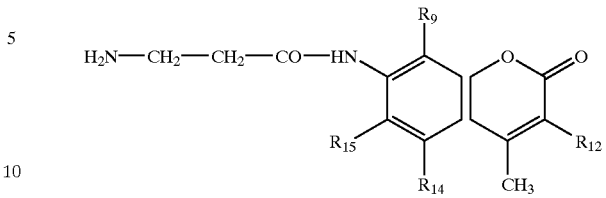

in which $R_9$, $R_{12}$, $R_{13}$, $R_{14}$ and $R_{15}$ represent an atom of hydrogen, bromine, chlorine or iodine, or a group such as —OH, —$CH_3$, —$CH_2CH_3$, —$OCH_3$, —$OCH_2CH_3$ or COOH at each of these positions. This type of substrate does not lend itself to use in semi-solid media and is more commonly used in liquid broth.

The third family of substrates is constituted by β-Alanyl-4-amino-2,6-dichlorophenol in which the marker part is 2,6-Dichloroaminophenol which has the following formula:

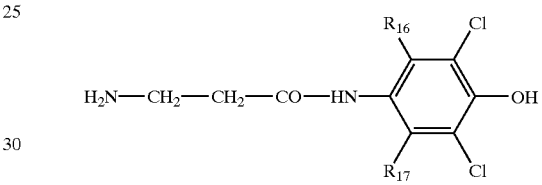

in which $R_{16}$ and $R_{17}$ represent an atom of hydrogen, bromine, chlorine or iodine, or a group such as —OH, —$CH_3$, —$CH_2CH_3$, —$OCH_3$, —$OCH_2CH_3$ or COOH at each of these positions. This type of compound has already been covered in patent application WO-A-99/51767, filed by the applicant, and requires the presence of a dry developer such as 3,5 Dihydroxy-2-naphthoic acid. This same patent application (WO-A-99/51767) also shows that it is possible to use other compounds in which the two chlorine atoms and the hydroxyl group are substituted by an atom of hydrogen, bromine, chlorine or iodine, or a group such as —OH, —$CH_3$, —$CH_2CH_3$, —$OCH_3$, —$OCH_2CH_3$ or COOH at each of these positions.

The fourth family of substrates is based on β-Alanyl p-nitroanilide and its derivatives in which p-Nitroaniline acts as the marker part. The general formula for this type of substrate is:

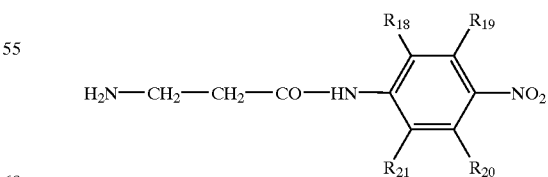

in which $R_{18}$, $R_{19}$, $R_{20}$ and $R_{21}$ represent an atom of hydrogen, bromine, chlorine or iodine, or a group such as —OH, —$CH_3$, —$CH_2CH_3$, —$OCH_3$, —$OCH_2CH_3$ or COOH at each of these positions. This product does not require the presence of any developer.

In the fifth family of substrates, 2-Amino-indole or 3-Amino-indole acts as the marker part. These substrates have the following formulae: for 2-Amino-indole:

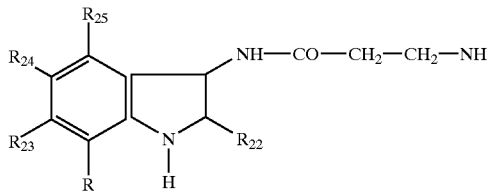

and for 3-Amino-indole:

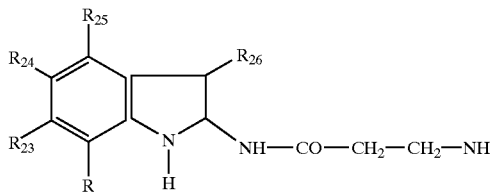

All these substrates are chromogenic apart from the second family which is fluorescent, and all correspond to compounds which can be used to identify the activity of the β-alanine aminopeptidase of *Pseudomonas aeruginosa*. This parameter can be used to clearly distinguish this pathogen from other, closely related species of Gram negative bacilli in a clinical setting.

1°) Substrates Used:

The enzyme substrates used had the following formula:

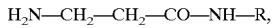

in which $H_2N-CH_2-CH_2-COOH$ is β-Alanine, i.e. the target part of the substrate; and $-NH_2-R$ is chromogenic, i.e. the marker part of said substrate.

Four substrates were tested, corresponding to the first four families of substrates mentioned above. They were:

β-Alanyl-β-naphtylamide, which is commercially available as product reference K1035 from the Bachem company (Bubendorf, Switzerland), β-Alanyl-7-amido-4-methylcoumarin, which is commercially available as product reference I1030 from the Bachem company (Bubendorf, Switzerland), β-Alanyl-4-amino-2,6-dichlorophenol, the synthetic pathway for which is given below, and β-Alanine p-nitroanilide, the synthetic pathway for which is given below.

β-Alanyl-4-amino-2,6-dichlorophenol was synthesized from N-Tert-butoxycarboxyl-β-alanine (1.89 g, 10 mmol). The N-Tert-butoxycarboxyl-β-alanine was dissolved in anhydrous Tetrahydrofurane (HPLC grade, 30 ml). The resultant solution was cooled to 0° C. in a ice-salt bath, and then N-methylmorpholine (2.02 g, 20 mmol) was added. The temperature was lowered to below −10° C. before slowly adding Isobutyl chloroformate (2.74 g, 20 mmol) without letting the temperature rise above −8° C. To the resultant anhydrous suspension was then added a cold solution of 4-Amino-2,6-dichlorophenol (1.78 g, 10 mmol) dissolved in Dimethylformamide and treated with N-methylmorpholine (4.08 g, 40 mmol) to release the free base. This solution was kept below room temperature before the above-mentioned addition operation. The resultant reaction mixture was stirred in an ice-salt bath for one hour, and thereafter at room temperature for a further five hours. Thin layer chromatography showed that conversion to the amide was almost 100%. The suspension was filtered to remove the N-Methylmorpholine hydrochloride and the residue was washed by adding Tetrahydrofurane. Next, the tetrahydrofurane and some of the dimethylformamide were removed using a rotary evaporator and the resultant solution was poured into icy water with vigorous shaking. The gray precipitate was recovered, thoroughly washed and dried in a vacuum oven at 30–40° C. After recrystallization from methanol with a little added water, the yield was 1.72 g of small, white crystals. This product was N-β-t-BOC-β-alanyl-4-amino-2,6-dichlorophenol which was subsequently dissolved in the smallest possible volume of hydrochloric acid-saturated Ethyl acetate. After two hours at about 16° C., the viscous solution was gently poured into 250 ml of anhydrous Diethyl ether. After four hours, the powdery solid was recovered by vacuum filtration and then washed in Diethyl ether. Finally, the product was dried in a vacuum drier and stored in a tightly closed container in order to prevent it absorbing moisture.

β-Alanine p-nitroanilide was synthesized in the following way. A mass of 2.76 grammes (g), i.e. 20 millimoles (mmol) of 4-Nitroaniline was dissolved by shaking in 40 milliliters (ml) of dry pyridine which had been cooled to below 12° C. In parallel, Phosphorus trichloride (1 ml redistilled) was added to 12 ml of pyridine (also at a temperatuere of below 12° C.). Both solutions were then cooled to below 16° C., and then the Phosphorus trichloride-containing solution was added with shaking to the Nitroaniline-containing solution. Mixing was carried out at a temperature of between below 14 and below 16° C. for at least 30 minutes (min) and then for the same amount of time at room temperature. Next, dry Benzyloxycarbonyl-β-Alanine (20 mmol, i.e. 4.46 g) was added stepwise over at least 5 min to the resultant solution, stirring throughout. Stirring was maintained for 14 hours (h) at between 30 and 40° C. Subsequently, the temperature was raised to 50° C. and stirring continued for a further 8 h. Thin layer chromatography of a diluted sample showed that most of the starting materials had been converted into the β-aminoacyl derivative. The pyridine was removed by rotary evaporation at 50° C. and the residual viscous oil was shaken vigorously with crushed ice and ethanol. This yielded a yellowish solid, some of which was deposited on the walls of the vessel, the rest making up, a crystalline mass. The solid was recovered, filtered with aspiration and washed with water. The product was air-dried and recrystallized from hot ethanol. The dry product weighed 4.3 g and was shown to be pure by thin layer chromatography (TLC) using silica gel plates (with ethyl acetate-toluene as the solvent). The yield was 62.7%. The protection constituted by the Benzyloxycarbonyl, present in the Benzyloxycarbonyl-β-alanine-p-nitroanilide, was then removed. To do this, 2.15 g of this material were dissolved in the smallest possible volume of hot glacial acetic acid with stirring. After this mixture had been cooled down to 25° C., an equal volume of 30% hydrobromic acid in glacial acetic acid was added with stirring. After 1 h 30 min, the resultant viscous solution was slowly poured into 400 ml of anhydrous Diethyl ether, with vigorous stirring throughout. The resultant white suspension was filtered and the residue washed with several aliquots of anhydrous ether before drying overnight in a vacuum drier. The yield was 1.50 g of β-Alanine-p-nitroanilide in the form of the bromide salt.

2°) Detection of β-Alanine Aminopeptidase Enzyme Activity Using Various Enzyme Substrates A—Testing β-Alanyl-β-naphthylamide and the Selectivity of its Target Part:

A number of species (a total of five strains per species unless otherwise specified) were tested in the presence of β-alanyl-β-naphthylamide using APIZYM-type test strips from bioMérieux (La Balme, France). Experiments were carried out with bacterial suspensions at a density of 4 McFarland units (McF) in phosphate buffer (0.01 M, pH 7.5). On the McFarland Scale which measures bacterial density, 4 McF corresponds to $12.10^8$ bacteria per milliliter. For every strain tested, 80 microliters of the relevant suspension were added to each well on a strip. The strips were incubated at 37° C. for 4 h. The presence of β-alanine aminopeptidase was detected by adding a drop of ZYMB (Fast Blue BB, a diazonium salt) which was obtained from bioMérieux (Product Reference 70480). If the reaction was positive, the solution turned orange. The results were as follows. The species in the following list all gave a negative result, i.e. no β-alanine aminopeptidase activity was detected in the following species:

Escherichia coli,
Shigella spp. (4 strains),
Shigella sonnei,
Edwarsiella tarda (2 strains),
Salmonella choleraesuis,
Salmonella typhi,
Salmonella spp.,
Salmonella paratyphi A,
Salmonella gallinarum (3 strains),
Salmonella arizonae,
Citrobacter freundii,
Citrobacter diversus,
Klebsiella pneumoniae, spp. pneumoniae,
Klebsiella pneumoniae, spp. oxytoca,
Klebsiella ozaenae,
Klebsiella rhinoscleromatis (3 strains),
Hafnia alvei,
Enterobacter aerogenes,
Enterobacter cloacae,
Enterobacter sakazakii,
Enterobacter gergoviae,
Serratia marcescens,
Serratia odorifera,
Serratia fonticola,
Serratia plymuthica,
Proteus vulgaris,
Proteus mirabilis,
Proteus morganii,
Proteus rettgeri,
Providencia alcalifaciens,
Providencia stuartii,
Yersinia enterocolitica,
Yersinia pseudotuberculosis,
Pseudomonas putida,
Comamonas acidovorans,
Comamonas testosteroni,
Pseudomonas alcaligenes,
Pseudomonas stutzeri,
Shewanella putrefaciens,
Stenotrophomonas maltophilia,
Brevundimonas diminuta,
Brevundimonas vesicularis,
Ralstonia picketti,
Pseudomonas luteola,
Pseudomonas oryzihabitans,
Sphingomonas paucimobilis,
Sphingobacterium multivorum,
Alcaligenes faecalis/odorans,
Achroniobacter xylosoxidans spp. denitrificans,
Achromobacter xylosoxidans, spp. xylosoxidans,
Bordetella bronchiseptica,
Oligella ureolytica (2 strains),
CDC IV $C_2$,
Aeromonas hydrophila,
Plesiomonas shigelloïdes,
Vibrio alginolyticus,
Vibrio parahaemolyticus (4 strains),
Chryseobacterium meningosepticum,
Empedobacter brevis (3 strains),
Chryseobacterium balustinum (1 strain),
Chryseobacterium indologenes,
Weeksella virosa (4 strains),
Myroïdes spp.,
Pasteurella gallinarum (1 strain),
Pasteurella multocida,
Pasteurella pneumotropica (4 strains),
Actinobacillus ureae (1 strain),
Pasteurella haemolytica,
Pasteurella aerogenes,
proches de Pasteurella (4 strains),
Psychrobacter phenylpyruvicus (4 strains),
Moraxella paraphenylpyruvica (3 strains),
Moraxella lacunata (4 strains),
Moraxella lac. sp. liquefaciens (7 strains),
Moraxella non liquefaciens (13 strains),
Moraxella bovis (4 strains),
Moraxella osloensis (18 strains), and
Actinobacillus spp.

In contrast, the species in the following list all gave a positive result, i.e. β-alanine aminopeptidase activity was detected in the following species:

Serratia liquefaciens,
Pseudomonas aeruginosa,
Pseudomonas fluorescens,
Burkholderia cepacia,
Pseudomonas mendocina., and
Ochrobactrum anthropi.

CDC is an acronym for the Center for Disease Control. CDC classifications concern groups of strains which have not yet been assigned a species name.

Therefore, the substrate β-alanyl -β-naphthylamide and specifically its target part β-alanine-is highly selective in that only six (6) species out of the seventy nine (79) tested (i.e. a fraction of only 7.1%) were found to posses β-alanine aminopeptidase activity.

On semi-solid medium, Pseudomonas aeruginosa can easily be distinguished from the other five species which give a positive result by virtue of the green tint of its colonies (which is due to the production of pyoverdine).

B—Testing Substrate β-Alanyl-7-amido-4-methylcoumarin and Assessing its Efficacy with Respect to the Detection of Strains of Pseudomonas aeruginosa:

The substrate β-Alanyl-7-amido-4-methylcoumarin was tested in the following way. Strains were isolated using the following media from bioMérieux (France):
Columbia Sheep's Blood,
Trypticase Soy with Sheep's Blood, and
MacConkey (used to isolate enteric bacilli).

The experiments were carried out using Vitek 2 cards (Registered Trademark, bioMérieux, Saint Louis, Mo., United States of America) with bacterial suspensions adjusted to a density of between 0.375 and 0.750 McF.

Table 1 below shows the usefulness of the substrate tested for some of the species dealt with in the preceding section, as well as for some other species (e.g. *Ochrobactrum anithropi*).

Simple tests such as the Arginine Hydrolysis or Acetamide Tests can be used to distinguish between *Pseudomonas aeruginosa* and *Ochrobactrum anthropi*.

TABLE 1

Efficacy of the substrate β-Alanyl-7-amido-4-methylcoumarin

| SPECIES | Number of strains tested | Number of negative results | Number of positive results | Borderline results |
|---|---|---|---|---|
| Shigella boydii | 10 | 10 | 0 | 0 |
| Shigella dysenteriae | 10 | 10 | 0 | 0 |
| Shigella flexneri | 10 | 10 | 0 | 0 |
| Chromobacterium violaceum | 11 | 9 | 1 | 1 |
| Chryseobacterium indologenes | 10 | 10 | 0 | 0 |
| Ochrobactrum anthropi | 11 | 0 | 11 | 0 |
| Oligella urethralis | 10 | 10 | 0 | 0 |
| Pseudomonas aeruginosa | 137 | 2 | 134 | 1 |
| Ralstonia pickettii | 10 | 8 | 2 | 0 |
| Pseudomonas mendocina | 10 | 0 | 10 | 0 |
| Pseudomonas stutzeri | 10 | 10 | 0 | 0 |
| Comamonas testoteroni | 10 | 10 | 0 | 0 |

Therefore, the substrate β-Alanyl-7-amido-4-methylcoumarin is particularly effective when it comes to detecting the following species:

*Ochrobactrum anthropi*, since the percentage of positive results is 100%,

*Pseudomonas aeruginosa*, since the percentage of positive results is 97.8%, and

*Pseudomonas mendocina*, since the percentage of positive results is 100%,

The efficacy with respect to *Pseudomonas aeruginosa* is of particular interest because a total of 137 strains were tested. The fact that three strains gave either a negative or a borderline result is due to biological variation within this species.

Some strains of other species were found to be able to hydrolyze β-Alanyl-7-amido-4-methylcoumarin, namely:

*Ralstonia pickettii*, since the percentage of positive results is 20%, and

*Chromobacterium violaceum*, since the percentage of positive results is 10%,

C—Testing substrate β-Alanyl-4-amino-2,6-dichlorophenol and Assessing its Efficacy with Respect to the Detection of Strains of *Pseudomonas aeruginosa:*

After isolation on Columbia Sheep's Blood agar, strains were tested on Vitek 2 cards (Registered Trademark, bioMérieux, Saint Louis, Mo., United States of America) in broth containing the substrate β-Alanyl-4-amino-2,6-dichlorophenol together with 3,5-dihydroxy-2-naphtoique and peptone, buffered to pH 8.5. The bacterial suspensions used were at a density of 0.5 McF in saline (4.5 g NaCl/liter). Results were read visually after 22 to 24 hours of incubation.

The results of these experiments are presented in Table 2 below.

TABLE 2

Efficacy of the substrate β-Alanyl-4-amino-2,6-dichlorophenol

| SPECIES | Number of strains tested | Number of negative results | Number positive results |
|---|---|---|---|
| Citrobacter amalonaticus | 2 | 2 | 0 |
| Citrobacter freundii | 2 | 2 | 0 |
| Citrobacter koseri | 1 | 1 | 0 |
| Enterobacter aerogenes | 2 | 2 | 0 |
| Enterobacter cloacae | 2 | 2 | 0 |
| Enterobacter intermedius | 1 | 1 | 0 |
| Escherichia coli | 2 | 2 | 0 |
| Proteus mirabilis | 2 | 2 | 0 |
| Proteus vulgaris | 1 | 1 | 0 |
| Providencia stuartii | 1 | 1 | 0 |
| Salmonella arizonae | 1 | 1 | 0 |
| Serratia liquefaciens | 1 | 0 | 1 |
| Serratia marcescens | 3 | 0 | 3 |
| Klebsiella oxytoca | 2 | 2 | 0 |
| Klebsiella pneumoniae | 3 | 3 | 0 |
| Achromobacter xylosoxydans | 2 | 2 | 0 |
| Acinetobacter baumannii | 2 | 2 | 0 |
| Aeromonas hydrophila | 2 | 2 | 0 |
| Brevundimonas diminuta | 2 | 2 | 0 |
| Burkholderia vesicularis | 1 | 1 | 0 |
| Chryseobacterium meningosepticum | 2 | 2 | 0 |
| Ochrobactrum anthropi | 1 | 0 | 1 |
| Moraxella non liquefaciens | 2 | 2 | 0 |
| Myroïdes spp. | 1 | 1 | 0 |
| Pseudomonas aeruginosa | 13 | 0 | 13 |
| Pseudomonas fluorescens | 2 | 1 | 1 |
| Pseudomonas mendocina | 1 | 0 | 1 |
| Pseudomonas putida | 1 | 1 | 0 |
| Pseudomonas stutzeri | 3 | 3 | 0 |
| Ralstonia pickettii | 1 | 1 | 0 |
| Shewanella algae | 1 | 1 | 0 |
| Shewanella putrefaciens | 1 | 1 | 0 |
| Sphingomonas paucimobilis | 2 | 2 | 0 |
| Stenotrophomonas maltophilia | 2 | 2 | 0 |
| Streptococcus agalactiae | 1 | 1 | 0 |
| Streptococcus pyogenes | 2 | 2 | 0 |
| Enterococcus faecalis | 2 | 2 | 0 |
| Enterococcus faecium | 2 | 2 | 0 |
| Vibrio vulnificus | 1 | 1 | 0 |

With this substrate, β-Alanyl-4-amino-2,6-dichlorophenol, the results for *Pseudomonas aeruginosa*, *Serratia liquefaciens*, *Serratia marcescens* were still significant, and those for *Pseudomonas mendocina* and *Ochrobactrum anthropi* fairly so. It may therefore be useful to combine this substrate with another one which makes it possible to distinguish *Pseudomonas aeruginosa* from other microorganisms which give a positive reaction (see paragraph 3). The pattern observed with *Pseudomonas fluorescens* is difficult to interpret and may be due to either methodological problems or genetic variability in this species.

Moreover, it should be noted that the presence of polyvinyl pyruvate (PVP) deepens the color in a positive reaction.

D—Testing Substrate β-Alanyl Para-nitroanilide:

Substantially the same methods were used as those described in the previous Paragraph C except that the visual read-out was performed after 19 hours. The substrate used was β-Alanyl p-nitroanilide. The results are summarized in Table 3 below.

TABLE 3

Efficacy of the substrate β-Alanyl-p-nitroanilide

| SPECIES | Number of strains tested | Number of negative results | Number positive results |
|---|---|---|---|
| Citrobacter amalonaticus | 2 | 2 | 0 |
| Citrobacter freundii | 2 | 2 | 0 |
| Citrobacter koseri | 1 | 1 | 0 |
| Enterobacter aerogenes | 2 | 2 | 0 |
| Enterobacter cloacae | 2 | 2 | 0 |
| Enterobacter intermedius | 1 | 1 | 0 |
| Escherichia coli | 2 | 2 | 0 |
| Proteus mirabilis | 2 | 2 | 0 |
| Proteus vulgaris | 1 | 1 | 0 |
| Providencia stuartii | 1 | 1 | 0 |
| Salmonella arizonae | 1 | 1 | 0 |
| Serratia liquefaciens | 1 | 0 | 1 |
| Serratia marcescens | 1 | 0 | 1 |
| Klebsiella oxytoca | 2 | 2 | 0 |
| Klebsiella pneumoniae | 2 | 2 | 0 |
| Achromobacter xylosoxydans | 2 | 2 | 0 |
| Acinetobacter baumannii | 2 | 2 | 0 |
| Aeromonas hydrophila | 2 | 2 | 0 |
| Brevundimonas diminuta | 1 | 1 | 0 |
| Burkholderia vesicularis | 1 | 1 | 0 |
| Chryseobacterium meningosepticum | 1 | 1 | 0 |
| Moraxella non liquefaciens | 2 | 2 | 0 |
| Myroïdes spp. | 1 | 1 | 0 |
| Pseudomonas aeruginosa | 4 | 0 | 4 |
| Pseudomonas putida | 1 | 1 | 0 |
| Pseudomonas stutzeri | 3 | 3 | 0 |
| Ralstonia pickettii | 1 | 1 | 0 |
| Shewanella algae | 1 | 1 | 0 |
| Sphingomonas paucimobilis | 2 | 2 | 0 |
| Stenotrophomonas maltophilia | 2 | 2 | 0 |
| Vibrio vulnificus | 1 | 1 | 0 |

These results are very revealing because *Pseudomonas aeruginosa* is easily distinguished from other species which do not possess β-alanine aminopeptidase activity.

Therefore, substrates with a target part consisting of β-Alanine designed to detect β-alanine aminopeptidase activity are ideal for detecting *Pseudomonas aeruginosa*, and a few other species (*Serratia liquefaciens, Pseudomonas marcescens, Pseudomonas mendocina* and *Ochrobactrum anthropi*) which are far less commonly encountered in test samples. In consequence, detection of this enzyme activity will most often be associated with the presence of *Pseudomonas aeruginosa* in the biological material being tested. It is nevertheless possible—as will be described in the next Paragraph—to distinguish *Pseudomonas aeruginosa* from any of these other species which possess β-alanine aminopeptidase activity.

3°) Concomitant Use of Two Enzyme Substrates To Assay Two Different Enzyme Activities, One Of Which Is That Of β-Alanine Aminopeptidase:

Using two substrates to assay two different enzyme activities is particularly useful. For example, the two different activities might be those of β-glucosidase and β-alanine aminopeptidase.

As mentioned in Example A in Chapter 2, the two different species *Pseudomonas aeruginosa* and *Pseudomonas mendocina* both express β-alanine aminopeptidase activity. These two species can however be distinguished by assaying for β-glucosidase activity which is only expressed by *Pseudomonas mendocina*. This activity can, for example, be assayed using the substrate 6-Chloro-3-indolyl-β-D-glycopyranoside which can be obtained from Biosynth (Staad, Switzerland).

These two species can be distinguished on semi-solid medium, as described in the following.

Trypticase Soy agar was supplemented with the following:
200 mg of 6-Chloro-3-indolyl-β-D-glycopyranoside,
50 mg of β-Alanyl-N,N'-dimethyl-p-phenylene-diamine, and
15 mg of 3,5-Dihydroxy-2-naphthoic acid.

The medium was poured out and inoculated as follows:
10 dishes with pure cultures corresponding to five strains of *Pseudomonas aeruginosa* and five of *Pseudomonas mendocina*, and
2 dishes with a mixture of two strains, one being of *Pseudomonas aeruginosa* and the other of *Pseudomonas mendocina*.

The Petri dishes were incubated at 35–37° C. After 18–24 hours of incubation, the color of the colonies was recorded. Blue colonies with a blue halo correspond to *Pseudomonas aeruginosa* which only expresses alanine aminopeptidase activity; purple colonies with a blue halo correspond to *Pseudomonas mendocina* which expresses both β-alanine aminopeptidase and β-glucosidase activities.

Thus, even if they are mixed together in the same specimen, these two different species can be easily distinguished on the same semi-solid medium. This example illustrates how it is possible to combine together in the same reaction medium different substrates specific for different enzyme activities, including one according to this invention for the characterization of *Pseudomonas aeruginosa*.

What is claimed is:

1. An enzyme substrate comprising a target portion and a marker portion, said target portion and marker portion being separable by hydrolysis, said target portion being specific for the enzyme activity being assayed, such that said target portion is acted upon by the enzyme β-alanine aminopeptidase derived from at least one *Pseudomonas aeruginosa* microorganism, and the marker portion is a molecule which reveals whether a hydrolysis reaction has taken place or not, wherein said substrate has the formula:

H$_2$N—CH$_2$—CH$_2$—CO—NH—R, in which H$_2$N—CH$_2$—CH$_2$—CO is the target portion and —NH—R is the marker portion of the substrate.

2. The substrate of claim 1, wherein the marker portion is a fluorescent or chromogenic molecule.

3. The substrate of claim 1, wherein said target portion is not acted upon by an enzyme of *E. Coli*.

4. The substrate of claim 1, wherein the marker portion is selected from the group consisting of β-naphthylamine, an aminomethylcoumarin, an aminobenzene derivative, p-nitroaniline, 2-amino-indoxyl, and 3-amnino-indoxyl.

5. The substrate of claim 4, wherein said marker portion is 7-amino-4-methyl-coumarin.

6. The substrate of claim 4, wherein said marker portion is 4-amino-2, 6-dichlorophenol.

7. A formulation for detecting at least one strain and/or species of microorganism comprising
at least one enzyme substrate comprising a target portion and a marker portion, said target portion and marker portion being separable by hydrolysis, said target portion being specific for the enzyme activity being assayed, such that said target portion is acted upon by the enzyme β-alanine aminopeptidase derived from at least one *Pseudomonas aeruginosa* microorganism, and the marker portion is a molecule which reveals whether a hydrolysis reaction has taken place or not, wherein said substrate has the formula:

H$_2$N—CH$_2$—CH$_2$—CO—NH—R, in which $H_2N-CH_2-CH_2-CO-$ is the target portion and $-NH-R$ is the marker portion of the substrate, and a culture medium.

8. The formulation of claim 7, wherein said formulation is either in the form of a liquid broth or a semi-solid medium.

9. The formulation of claim 7, wherein the culture medium comprises a developer which is a diazonium salt when the marker portion released is β-naphthylamine, or the developer is 3, 5-dihydroxy-2-naphthoic acid when the marker portion released is an aminobenzene derivative.

10. The formulation of claim 9, wherein said aminobenzene derivative is dichloro-amino-phenol.

11. A formulation for detecting at least one strain and one species of microorganism, or at least two strains or two species of microorganism, comprising at least one enzyme substrate comprising a target portion and a marker portion, said target portion and marker portion being separable by hydrolysis, said target portion being specific for the enzyme activity being assayed, such that said target portion is acted upon by the enzyme β-alanine aminopeptidase derived from at least one *Pseudomonas aeruginosa* microorganism, and the marker portion is a molecule which reveals whether a hydrolysis reaction has taken place or not, wherein said substrate has the formula:

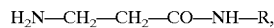

in which $H_2N-CH_2-CH_2-CO-$ is the target portion and $-NH-R$ is the marker portion of the substrate, a culture medium, and at least one other substrate.

12. A method for detection of *Pseudomonas aeruginosa*, comprising:

contacting at least one substrate capable of detecting β-alanine aminopeptidase enzyme activity with a sample suspected of containing at least one *Pseudomonas aeruginosa* microorganism, and monitoring for the appearance of a colored and/or fluorescent signal from said sample and which correlates to said β-alanine aminopeptidase enzyme activity.

wherein said substrate has the formula:

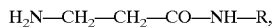

in which $H_2N-CH_2-CH_2-CO-$ is the target portion and $-NH-R$ is the marker portion of the substrate.

13. The method of claim 12, wherein said sample comprises a culture medium which is semi-solid.

14. The method of claim 13, wherein a compound is added to the culture medium to inhibit diffusion of colored and/or fluorescent molecules.

15. A method for detection of *Pseudomonas aeruginosa*, comprising:

contacting at least one substrate capable of detecting β-alanine aminopeptidase enzyme activity with a sample suspected of containing at least one *Pseudomonas aeruginosa* microorganism, contacting at least one substrate capable of detecting the activity of an enzyme other than β-alanine aminopeptidase with a sample suspected of containing at least one microorganism other than *Pseudomonas aeruginosa*, this other enzyme activity making it possible to distinguish *Pseudomonas aeruginosa* from said other microorganism, and monitoring for the appearance of a colored and/or fluorescent signal from said sample and which correlates to said β-alanine peptidase enzyme activity.

wherein said substrate has the formula:

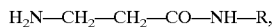

in which $H_2N-CH_2-CH_2-CO-$ is the target Portion and $-NH-R$ is the marker portion of the substrate.

* * * * *